United States Patent
Moshkovitz et al.

(10) Patent No.: US 11,135,169 B2
(45) Date of Patent: Oct. 5, 2021

(54) TECHNOLOGIES FOR MANAGING A TREATMENT PROGRAM USING SMART PILLS

(71) Applicant: Intel Corporation, Santa Clara, CA (US)

(72) Inventors: Ariel Moshkovitz, Haifa (IL); Glen J. Anderson, Beaverton, OR (US); Tamara Gaidar, Haifa (IL); Omer Ben-Shalom, Rishon Le-Tzion (IL); Jennifer A. Healey, San Jose, CA (US); Ido Lapidot, Haifa (IL)

(73) Assignee: Intel Corporation, Santa Clara, CA (US)

( * ) Notice: Subject to any disclaimer, the term of this patent is extended or adjusted under 35 U.S.C. 154(b) by 1302 days.

(21) Appl. No.: 14/998,209

(22) Filed: Dec. 26, 2015

(65) Prior Publication Data

US 2017/0185743 A1   Jun. 29, 2017

(51) Int. Cl.
*A61K 9/20*    (2006.01)
*A61K 9/00*    (2006.01)
(Continued)

(52) U.S. Cl.
CPC .............. *A61K 9/20* (2013.01); *A61K 9/0097* (2013.01); *G06Q 10/109* (2013.01);
(Continued)

(58) Field of Classification Search
CPC ... G06F 19/3456; G06F 19/325; G16H 10/60; A61K 9/20; A61K 9/0097; G06Q 10/109
See application file for complete search history.

(56) References Cited

U.S. PATENT DOCUMENTS

2006/0093785 A1   5/2006  Hickle
2006/0149339 A1   7/2006  Burnes et al.
(Continued)

OTHER PUBLICATIONS

International search report for PCT application No. PCT/US2016/063556, dated Mar. 20, 2017 (4 pages).
(Continued)

*Primary Examiner* — Linh Giang Le
(74) *Attorney, Agent, or Firm* — Hanley, Flight & Zimmerman, LLC

(57) ABSTRACT

Technologies for managing a treatment program include a treatment management server, smart pills, and patient computing devices. The treatment management server is configured to generate treatment data usable by the smart pills to control a release of one or more drugs in patients. The treatment management server is also configured to transmit the treatment data to the smart pills, obtain physiological data associated with the patients, identify a preferred physiological response among the patients based on the physiological data, and identify the treatment data associated with the preferred physiological response. The smart pills are configured to obtain the treatment data, release one or more drugs into the patients based on the treatment data, sense physiological conditions in the patients, and transmit the physiological conditions to the treatment management server. The patient computing devices facilitate communication between the treatment management server and the smart pills. Other embodiments are described.

25 Claims, 10 Drawing Sheets

(51) Int. Cl.
*G06Q 10/10* (2012.01)
*G16H 10/60* (2018.01)
*G16H 20/10* (2018.01)
*G16H 70/20* (2018.01)

(52) U.S. Cl.
CPC ............. *G16H 10/60* (2018.01); *G16H 20/10* (2018.01); *G16H 70/20* (2018.01)

(56) References Cited

U.S. PATENT DOCUMENTS

| | | |
|---|---|---|
| 2006/0206066 A1 | 9/2006 | Ferek-Petric |
| 2008/0077440 A1 | 3/2008 | Doron |
| 2010/0185055 A1* | 7/2010 | Robertson .......... G01N 27/3277 600/117 |
| 2013/0310664 A1* | 11/2013 | Kozloski ............... A61M 31/00 600/302 |
| 2015/0306313 A1 | 10/2015 | Baykal |

OTHER PUBLICATIONS

Written opinion for PCT application No. PCT/US2016/063556, dated Mar. 20, 2017 (8 pages).

"'Smart pill' that analyzes how whole gut is working as it passes through could ease IBS", downloaded from http"//www.dailymail.co.uk/health/article-2045643/IBS-Smart-pill-help-ease-irritable-bowel-analysing-gut-passes-through.html#xzz3QhZF4INc, retrieved May 26, 2016.

\* cited by examiner

TECHNOLOGIES FOR MANAGING A TREATMENT PROGRAM USING SMART PILLS

BACKGROUND

Conventional methods for treating illnesses, diseases, and other medical conditions generally involve a physician identifying symptoms exhibited or described by a patient and prescribing a drug in accordance with the symptoms. The patient may report back after a period of days with a subjective report on how the patient is feeling, or may not report back at all. Due to the subjective and imprecise nature of this process, it is difficult to pinpoint the exact causes of many medical conditions and to determine the effectiveness of any treatments.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
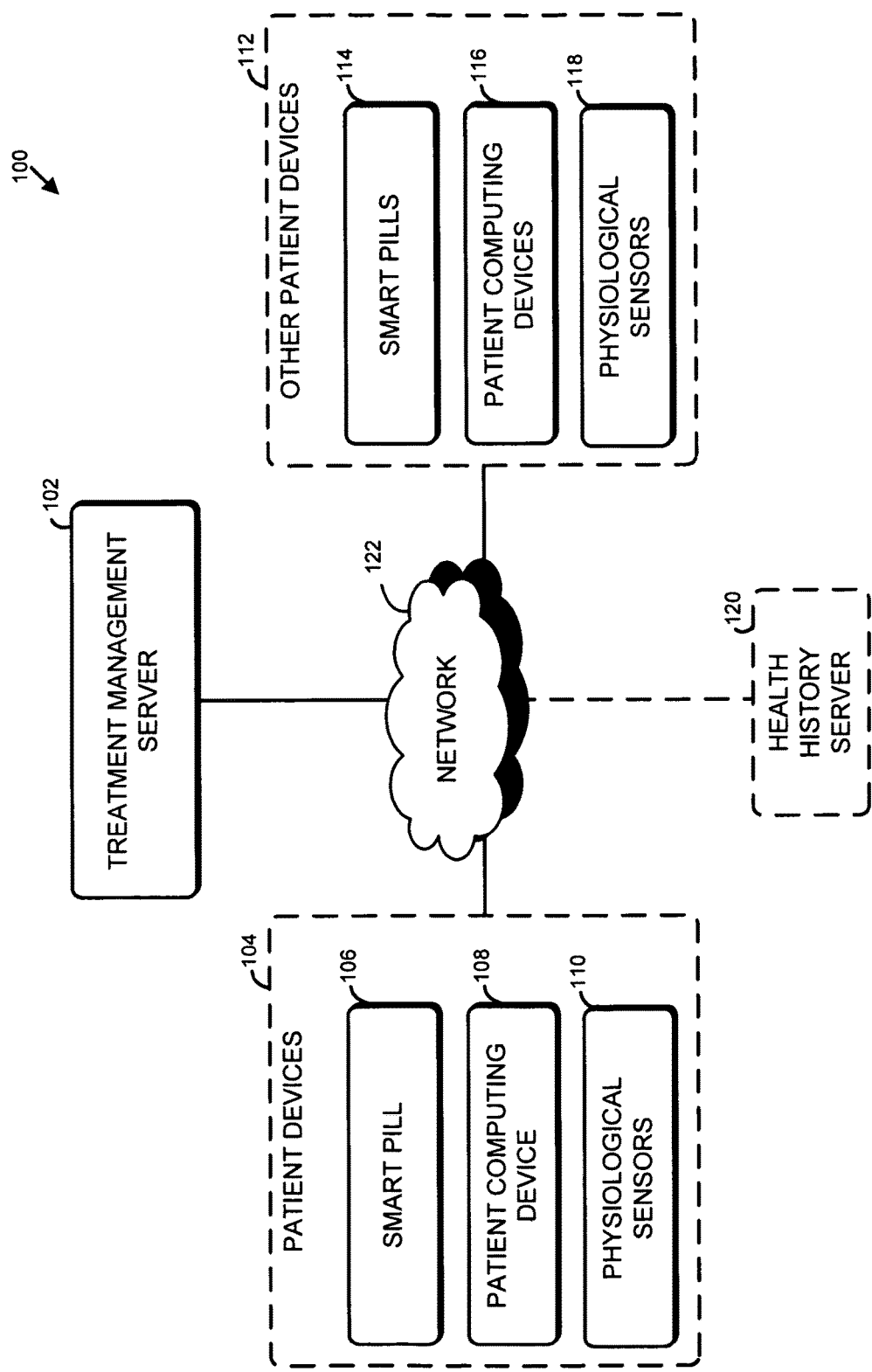
FIG. 1 is a simplified block diagram of at least one embodiment of a system for managing a treatment program using smart pills and patient computing devices.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in an illustrative embodiment, a system 100 for managing a treatment program includes a treatment management server 102, patient devices 104 associated with a patient, patient devices 112 associated with various other patients, and a health history server 120 in some embodiments, which may communicate with each other via a network 122. The patient devices 104 illustratively include one or more smart pills 106, a patient computing device 108, and physiological sensors 110. Likewise, the patient devices 112 associated with other patients include smart pills 114, patient computing devices 116, and physiological sensors 118. In use, as described in more detail herein, the treatment management server 102 is configured to generate treatment data that dictates how the smart pills 106 and 114, when consumed by patients, will release drugs into the patients. In the illustrative embodiment, the treatment data controls various aspects of the drug treatment program such as which drugs are to be released, how much of each drug is to be released, and when the drugs are to be released. Further, in the illustrative embodiment, the treatment management server 102 is configured to introduce variations in the treatment data, such that one smart pill (e.g., the smart pill 106) releases slightly different amounts of one or more drugs compared another smart pill (e.g., one of the smart pills 114). The treatment data may vary in terms of when the drugs are released by the smart pills 106 and 114 as well. Additionally, the treatment management server 102 is configured to obtain detailed patient physiological data from the smart pills 106 and 114, the physiological sensors 110 and 118, and the patient computing devices 108 and 116 regarding the patients who consumed the smart pills 106 and 114. The treatment management server 102 may subsequently determine which of the patients had a preferred (e.g., the best) physiological response to the treatments and update the treatment data for use by the other smart pills in the other patients. Accordingly, the treatment management server 102 refines the treatments using the detailed physiological data from the multiple patients.

As described in more detail herein, the smart pills 106 and 114 are configured to release drugs in accordance with the treatment data, monitor physiological characteristics of the patients who consumed the smart pills, and transmit the physiological data to the treatment management server 102 as patient physiological data. Further, as described in more detail herein, the physiological sensors 110 and 118 are configured to supplement the physiological data transmitted from the smart pills. Additionally, as described in more detail herein, the patient computing devices 108 and 116 are configured to facilitate communication between the treatment management server 102, the smart pills 106 and 114, and the physiological sensors 110 and 118.

Figure 2:
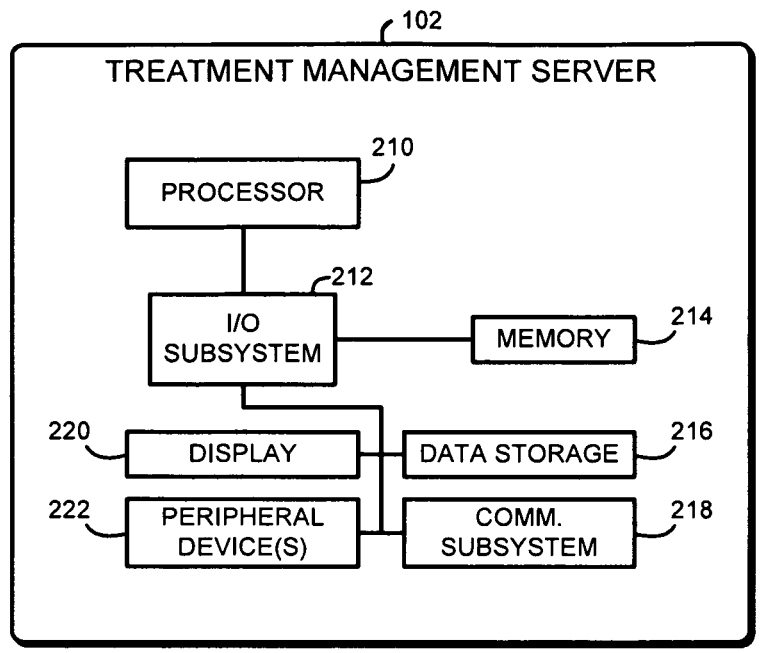
FIG. 2 is a simplified block diagram of at least one embodiment of a treatment management server of the system of FIG. 1.

Referring now to FIG. 2, the treatment management server 102 may be embodied as any type of server device capable of generating treatment data to control the release of drugs in patients, updating the treatment data based on received patient physiological data, and otherwise performing the functions described herein. For example, the treatment management server 102 may be embodied as, without limitation, a server computer, a distributed computing system, a networking device, a multiprocessor system, a consumer electronic device, a smart appliance, and/or any other computing device capable of performing the functions described herein. Although shown as a single computing device, it should be appreciated that the treatment management server 102 may be embodied as a collection of servers and/or other compute devices configured to cooperate to perform the functions described herein.

The illustrative treatment management server 102 includes a processor 210, an I/O subsystem 212, a memory 214, a data storage device 216, a communication subsystem 218, a display 220, and peripheral devices 222. Of course, the treatment management server 102 may include other or additional components, such as those commonly found in a workstation (e.g., various input/output devices), in other embodiments. Additionally, in some embodiments, one or more of the illustrative components may be incorporated in, or otherwise form a portion of, another component. For example, the memory 214, or portions thereof, may be incorporated in the processor 210 in some embodiments.

The processor 210 may be embodied as any type of processor capable of performing the functions described herein. For example, the processor 210 may be embodied as a single or multi-core processor(s), digital signal processor, microcontroller, or other processor or processing/controlling circuit. Similarly, the memory 214 may be embodied as any type of volatile or non-volatile memory or data storage capable of performing the functions described herein. In operation, the memory 214 may store various data and software used during operation of the treatment management server 102 such as operating systems, applications, programs, libraries, and drivers. The memory 214 is communicatively coupled to the processor 210 via the I/O subsystem 212, which may be embodied as circuitry and/or components to facilitate input/output operations with the processor 210, the memory 214, and other components of the treatment management server 102. For example, the I/O subsystem 212 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 212 may form a portion of a system-on-a-chip (SoC) and be incorporated, along with the processor 210, the memory 214, and other components of the treatment management server 102, on a single integrated circuit chip.

The data storage device 216 may be embodied as any type of device or devices configured for short-term or long-term storage of data such as, for example, memory devices and circuits, memory cards, hard disk drives, solid-state drives, or other data storage devices. The data storage device 216 may store, for example, received patient physiological data, patient schedule data, health history data, and heuristics for determining treatment data based on the afore-mentioned data.

The communication subsystem 218 may be embodied as any communication circuit, device, or collection thereof, capable of enabling communications between the treatment management server 102 and other remote devices over a computer network (e.g., the network 122). The communication subsystem 218 may be configured to use any one or more communication technology (e.g., wired or wireless communications) and associated protocols (e.g., Ethernet, Bluetooth®, Wi-Fi®, WiMAX, etc.) to effect such communication.

Additionally, the treatment management server 102 may include a display 220 that may be embodied as any type of display capable of displaying digital information such as a liquid crystal display (LCD), a light emitting diode (LED), a plasma display, a cathode ray tube (CRT), or other type of display device. In some embodiments, the treatment management server 102 may also include one or more peripheral devices 222. The peripheral devices 222 may include any number of additional input/output devices, interface devices, and/or other peripheral devices.

Figure 3:
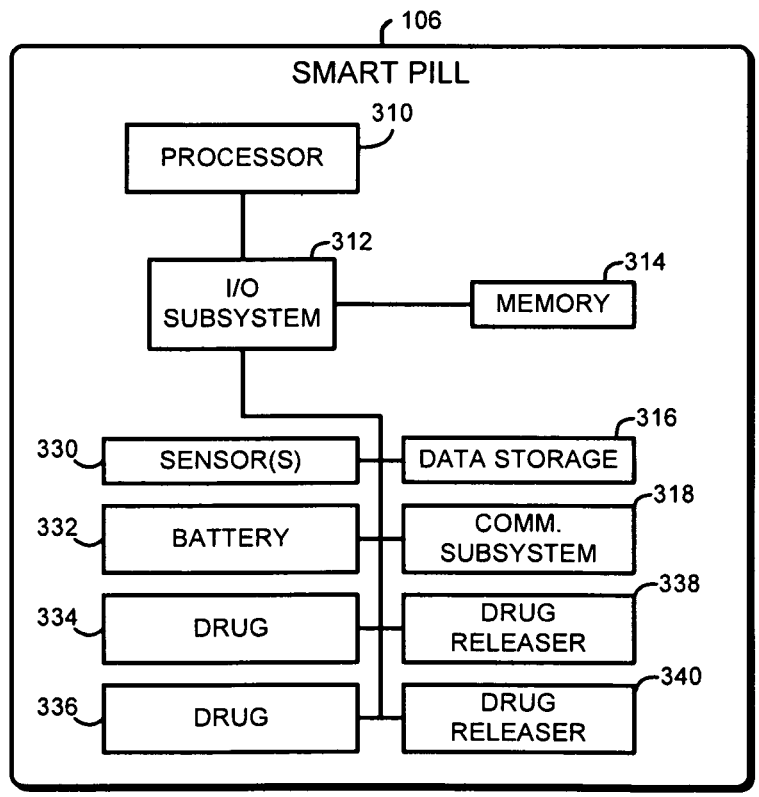
FIG. 3 is a simplified block diagram of at least one embodiment of a smart pill of the system of FIG. 1.

Referring now to FIG. 3, the smart pill 106, 114 may be embodied as any device capable of being consumed or otherwise placed inside a patient's body, releasing one or more drugs in accordance with treatment data generated by the treatment management server 102, and sensing and reporting physiological conditions within the body as described in more detail herein. Although the description below is provided with reference to smart pill 106, it should be appreciated that such description is equally applicable to the smart pills 114 of the other patient devices 112.

In the illustrative embodiment, the smart pill 106 includes a processor/microcontroller 310, an I/O subsystem 312, a memory 314, a data storage device 316, and a communication subsystem 318. Those components may be substantially similar to the corresponding components of the treatment management server 102. In at least some embodiments, the components are scaled down to accommodate the smaller physical size of the smart pill 106 relative to the size of the treatment management server 102. For example, in some embodiments, many or all of the components of the smart pill 106, 114 may be embodied on a common die such as a system-on-a-chip (SoC). Regardless, further descriptions of the like components are not repeated herein with the understanding that the description of the corresponding components provided above in regard to the source computing device 102 applies equally to the corresponding components of the destination computing device 106.

The illustrative smart pill 106 includes various sensors 330, a battery 332, various drugs 334 and 336, and corresponding drug releasers 338 and 340. The sensors 330 may include, or otherwise be embodied as any type of sensor capable of sensing a physiological characteristic of the patient. For example, in some embodiments, the sensors 330 may include a visual sensor such as a camera, a pH level sensor to measure acidity in the body, a protein sensor to detect various proteins in the body, and/or a chemical sensor to detect the presence of and amounts of various chemicals in the body. In the illustrative embodiment, the battery 332 may be embodied as any one or more devices capable of storing energy and providing the stored energy to the other components of the smart pill 106, as needed.

As discussed above, the smart pill 106 is configured to administer the drugs 334, 336 according to the treatment data. Although shown in FIG. 3 as including the two drugs 334, 336, it should be appreciated that the smart pill 106 may include only one drug in some embodiments or more than two drugs in other embodiments. In the illustrative embodiment, the drugs 334 and 336 are different from each other and are stored in reservoirs within the smart pill 106, but may be similar or identical drugs in other embodiments. The drugs 334 and 336 may include, but are not limited to fluids, solids, organic material, inorganic material, vitamins, and/or microbots. The corresponding drug releasers 338 and 340 may be embodied as any type of mechanical or electromechanical devices, such as pumps, that are configured to release specified amounts of the drugs 338 and 340 in accordance with the treatment data. More specifically, in the illustrative embodiment, the drug releasers 338 and 340 are configured to be controlled by the processor 310 to release the drugs 334 and 336 in accordance with the treatment data.

Referring back to FIG. 1, the health history server 120 may be embodied as any type of server computer capable of maintaining health history data related to the patients. The maintained health history data may include any type of health-related information associated with patients including, but not limited to, allergies, drug reactions, physiological characteristics, health concerns/issues, drug prescription history, and/or the like. The health history server 120 may include components commonly found in a server computer, such as a processor, memory, I/O subsystem, data storage, communication subsystem, etc. Those components may be substantially similar to the corresponding components of the treatment management server 102. As such, further descriptions of the like components are not repeated herein with the understanding that the description of the corresponding components provided above in regard to the treatment management server 102 applies equally to the corresponding components of the health history server 120.

The physiological sensors 110 and 118 may be embodied as, or otherwise include, any type of sensor capable of sensing, obtaining, and/or generating sensor data indicative of a physiological characteristic of a patient or from which a physiological characteristic may be derived. For example, the illustrative physiological sensors 110 and 118 may monitor physiological characteristics of the patients, activities of the patients, characteristics of the patients' environments, and/or other factors indicative of or which can impact the patients' physiological characteristics. The illustrative patient physiological sensors 110 and 118 include wearable sensors, body fluid sensors, and/or environmental sensors. The wearable sensors may be embodied as any type of sensors capable of being worn by a patient and producing sensor data indicative of a physiological characteristic of the patient. For example, the wearable sensors may include, but are not limited to, a heart rate sensor, a blood pressure sensor, a brain activity sensor (e.g., an electroencephalogram (EEG) sensor and/or a functional near-infrared spectroscopy (fNIRS) sensor), a temperature sensor, a pedometer, and/or other sensors configured to be worn by the patient and to measure physiological conditions of the patient. The body fluid sensors may be embodied as any type of sensor or sensing device capable of analyzing a body fluid of a patient, such as waste fluids, saliva, or other substances from the patient's body to detect the presence of and/or amounts of medication, viruses, bacteria, sugar, or other items. For example, the body fluid sensors may be embodied as a smart toilet or sink, a blood monitoring device, a smart saliva stick, and/or the like. The environmental sensors may be embodied as any type of sensors capable of measuring various environmental characteristics of the environment of the patient. For example, the environmental sensors may include sensors associated with the weather (e.g., temperature sensors and pressure sensors), as well as sensors configured to detect the presence of and/or measure the amount of bacteria, viruses, chemicals, and/or other substances that may affect the health of the patient. Of course, the patient physiological sensors 110 and 118 may include additional or other types of sensors in other embodiments.

Each of the patient computing devices 108 and 116 may be embodied as any type of personal computing device, such as a smartphone, tablet, or other computing device, usable by a patient. Each of the patient computing devices 108 and 116 may include components commonly found in a computer, such as a processor, memory, I/O subsystem, data storage, communication subsystem, etc. Those components may be substantially similar to the corresponding components of the treatment management server 102. As such, further descriptions of the like components are not repeated herein with the understanding that the description of the corresponding components provided above in regard to the treatment management server 102 applies equally to the corresponding components of the patient computing devices 108 and 116. In some embodiments, each of the patient computing devices 108 and 116 may be embodied as a special-purpose computing device. In other embodiments, the patient computing devices 108 and 116 may be general-purpose devices, such as personal smartphones.

In the illustrative embodiment, each of the patient computing devices 108 and 116 may be to configured act as a communication link between the respective smart pills 106 and 114, the physiological sensors 110 and 118, and the treatment management server 102. For example, each patient computing device 108 and 116 may be configured to receive treatment data from the treatment management server 102 and transmit the treatment data to the respective smart pills 106 and 114 associated with the patients. Additionally, each patient computing device 108 and 116 may be configured to receive patient physiological data from the respective smart pills 106 and 114, as well as from the physiological sensors 110 and 118 associated with each patient, and transmit the patient physiological data to the treatment management server 102. In alternative embodiments, the smart pills 106 and 114 and/or the physiological sensors 110 and 118 may be configured to communicate directly with the treatment management server 102. In the illustrative embodiment, the patient computing devices 108 and 116 are configured to anonymize the patient physiological data before transmitting the patient physiological data to the treatment management server 102. In addition to potentially acting as a communication link, the patient computing devices 108 and 116 may be configured to present the patient physiological data to the respective patients for review. Further, the patient computing devices 108 and 116 may be configured to prompt the respective patients for authorization to share the patient physiological data and obtain authorization from the respective patients prior to transmitting the patient physiological data to the treatment management server 102. Accordingly, the patients may exercise control over whether their physiological data is shared.

As discussed above, the treatment management server 102, the patient devices 104 and 112, and the health history server 120 are each configured to communication over the network 122. The network 122 may be embodied as any number of various wired and/or wireless networks. For example, the network 122 may be embodied as, or otherwise include, a wired or wireless local area network (LAN), a wired or wireless wide area network (WAN), a cellular network, and/or a publicly-accessible, global network such as the Internet. As such, the network 122 may include any number of additional devices, such as additional computers, routers, and switches, to facilitate communications among the devices of the system 100.

Figure 4:
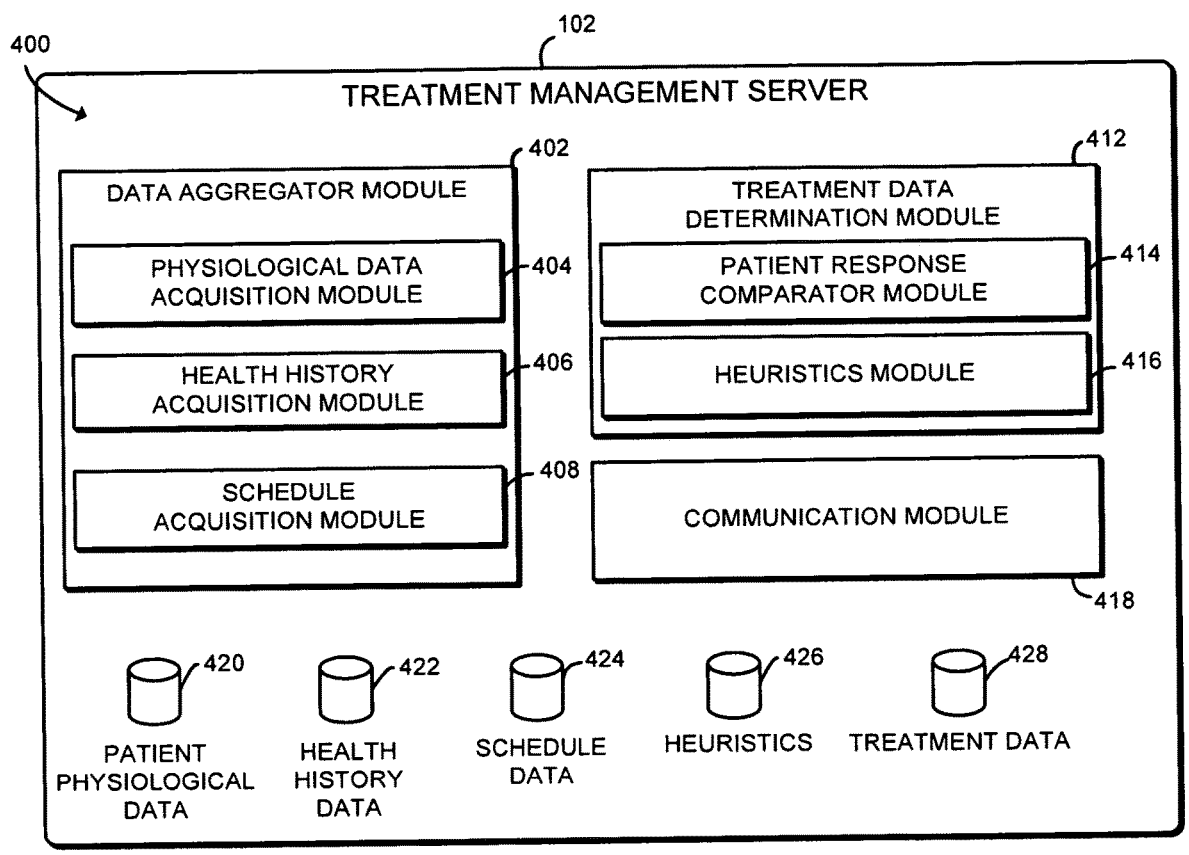
FIG. 4 is a simplified block diagram of at least one embodiment of an environment that may be established by the treatment management server of FIGS. 1 and 2.

Referring now to FIG. 4, in the illustrative embodiment, the treatment management server 102 establishes an environment 400 during operation. The illustrative environment 400 includes a data aggregator module 402, a treatment data determination module 412, and a communication module 418. Each of the modules, logic, and other components of the environment 400 may be embodied as hardware, software, firmware, or a combination thereof. For example, each of the modules, logic, and other components of the environment 400 may form a portion of, or otherwise be established by, the processor 210, the memory 214, the communication subsystem 218, and/or other hardware components of the treatment management server 102. As such, in some embodiments, one or more of the modules of the environment 400 may be embodied as circuitry or a collection of electrical devices (e.g., a data aggregator circuit 402, a treatment data determination circuit 412, a communication circuit 418, etc.).

The data aggregator module 402 is configured to aggregate data from multiple sources including the smart pills 106 and 114, the physiological sensors 110 and 118, the patient computing devices 108 and 116, and/or the health history server 120, pertaining to multiple patients. In the illustrative embodiment, the data aggregator module 402 includes a physiological data acquisition module 404, a health history acquisition module 406, and a schedule acquisition module 408. The physiological data acquisition module 404, in the illustrative embodiment, is configured to receive patient physiological data 420 generated by the smart pills 106 and 114 (e.g., pH levels, various protein levels, and/or various chemical levels), the physiological sensors 110 and 118 (e.g., heart rates, blood pressures, brain activity levels, body temperatures, bacteria levels, virus levels, etc.), and the patient computing devices 108 and 116 (e.g., subjective patient-reported opinions of their health statuses). The health history acquisition module 406 is configured to acquire health history data 422 for use by the data aggregator module 402. Additionally, the schedule acquisition module 408 is configured to obtain patient schedule data 424, such as scheduled activities (e.g., exercise, meetings, travel, etc.) at specified times and locations, that are indicative of types and levels of activity of the patients and environments the patients are exposed to. In acquiring data, such as the patient physiological data 420, the health history data 422, and the schedule data 424, the respective modules 404, 406, and 408 may poll the sources for the data, receive the data as it is pushed to the modules 404, 406, and 408, and/or store and retrieve the data from respective databases.

The treatment data determination module 412 is configured to determine types and amounts of drugs to be released by the smart pills 106 and 114, as well as when the drugs are to be released in the bodies of the respective patients. In other words, the treatment data determination module 412 is configured to generate the treatment data 428 for use by the smart pills 106 and 114. In the illustrative embodiment, the treatment data determination module 412 is configured to introduce variations in an initial set of the treatment data 428 to be transmitted to the respective smart pills 106 and 114 such that the respective patients receive differing types and/or amounts of drugs, possibly at different times. In the illustrative embodiment, the treatment data determination module 412 is also configured to generate and adjust or modify the treatment data 428 based on the patient physiological data 420, the health history data 422, and the schedule data 424. For example, in the illustrative embodiment, the treatment data determination module 412 is configured to generate a standard set of treatment data 428 and then adjust the treatment data 428 for each of the patients based on patient-specific factors, such as their health history data 422 and/or schedule data 424. More specifically, the treatment data determination module 412 may be configured to reduce an amount of a particular drug in view of a heightened sensitivity to the drug indicated in the health history data 422. As another example, the treatment data determination module 412 may be configured to increase an amount of a particular drug (e.g. a vitamin) based on an indication in the patient schedule data 424 that a patient likely receives an abnormally low level of sunlight based on their scheduled time indoors or in locations that typically receive relatively little sunlight.

In the illustrative embodiment, the treatment data determination module 412 includes a patient response comparator module 414 and a heuristics module 416. The patient response comparator module 414 is configured to analyze the patient physiological data 420 associated with each patient who has consumed one of the smart pills 106 and 114 and identify a preferred physiological response in the patient physiological data 420. More specifically, in the illustrative embodiment, the patient response comparator module 414 compares a physiological response associated with each patient in the received patient physiological data 420 to a target physiological response, representing a goal that the treatment is to achieve, such as a particular blood pressure. The patient physiological response that most closely matches the target physiological response is the preferred physiological response. The patient response comparator module 414 is also configured to identify the treatment data 428 associated with the preferred physiological response (i.e., the treatment data that was transmitted to the smart pill 106 or 114 associated with the preferred physiological response). The treatment data determination module 412 is configured to modify the treatment data associated with the various smart pills 106 and 114 toward the treatment data that resulted in the preferred physiological response. In this way, when the modified treatment data 428 is transmitted to the smart pills 106 and 114, the resulting physiological responses of all of the patients are likely to be closer to the target physiological response (i.e., the goal of the treatment program). In the illustrative embodiment, the heuristics module 416 is configured to apply one or more heuristics 426 to the data used by the treatment data determination module 412 to generate, adjust, and modify the treatment data 428 as described above.

The communication module 418 is configured to receive data from devices, such as the patient devices 104 and 112 and the health history server 120. Further, the communication module 418 is configured to transmit data, such as the treatment data 428, to the devices.

Figure 5:
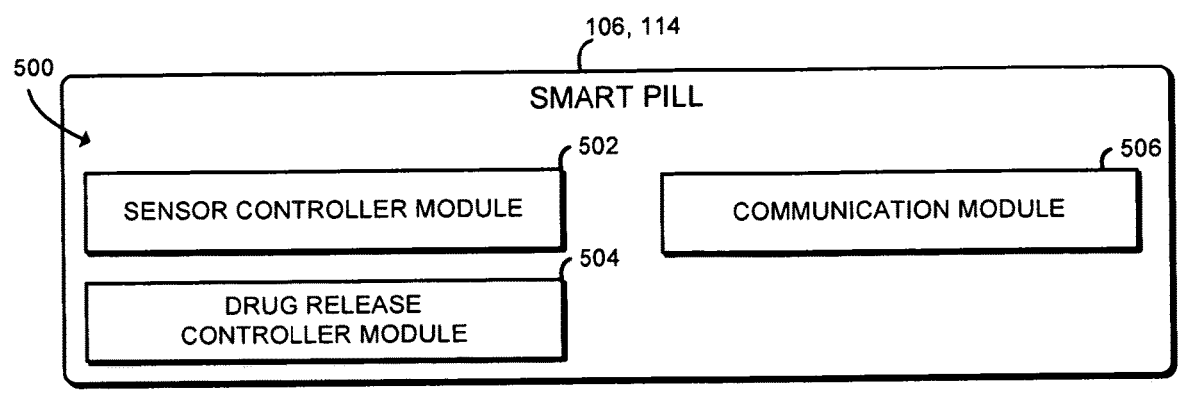
FIG. 5 is a simplified block diagram of at least one embodiment of an environment that may be established by a smart pill of FIGS. 1 and 3.

Referring now to FIG. 5, in the illustrative embodiment, the smart pill 206 establishes an environment 500 during operation. The illustrative environment 500 includes a sensor controller module 502, a drug release controller module 504, and a communication module 506. Each of the modules, logic, and other components of the environment 500 may be embodied as hardware, software, firmware, or a combination thereof. For example, each of the modules, logic, and other components of the environment 500 may form a portion of, or otherwise be established by, the processor 310, the memory 314, the communication circuitry 318, and/or other hardware components of the smart pill 106. As such, in some embodiments, one or more of the modules of the environment 500 may be embodied as circuitry or a collection of electrical devices (e.g., a sensor controller circuit 502, a drug release controller circuit 504, a communication circuit 508, etc.).

The sensor controller module 502 is configured to activate and control the sensors 330 in the smart pill 106 to detect and/or measure physiological conditions in the body of a patient who consumed the smart pill 106. For example, the sensor controller module 502 may be configured to control the sensors 330 to measure an acidity (i.e., a pH) of one or more body fluids in the patient, to determine types and amounts of proteins in the patient, to measure one or more chemicals in the patient, and/or to obtain images or video of internal portions of the patient, such as to identify signs of inflammation or irritation.

The drug release controller module 504 is configured to activate and control the drug releasers 338 and 340 in accordance with the treatment data 428. For example, the drug release controller module 504 may be configured to interpret the treatment data 428 to identify parameters including drug types to be released, amounts of the drugs to be released, and a release schedule (i.e., drug release times) and to control the corresponding drug releasers 338 and 340 to release one or more of the drugs 334 and 336 in accordance with the parameters.

The communication module 506 is configured to facilitate communications between the smart pill 106 and other devices of the system 100. In the illustrative embodiment, the communication module 506 is configured to receive the treatment data 428 from the patient computing device 108, such as through relatively short range wireless communication. In other embodiments, the communication module 506 is configured to receive the treatment data 428 directly from the treatment management server 102. Further, the communication module 502 is configured to transmit patient physiological data 420 to the patient computing device 108 or directly to the treatment management server 102, depending on the embodiment. It should be understood that the smart pills 114 include similar modules as those described above with reference to the smart pill 106.

Figure 6:
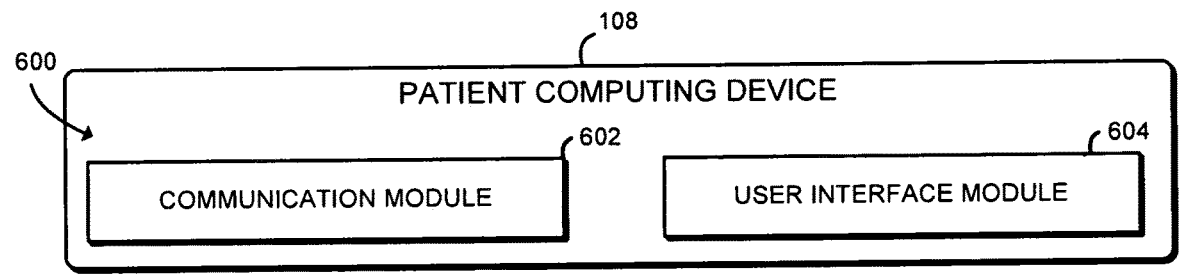
FIG. 6 is a simplified block diagram of at least one embodiment of an environment that may be established by a patient computing device of the system of FIG. 1.

Referring now to FIG. 6, in the illustrative embodiment, the patient computing device 108 establishes an environment 600 during operation. The illustrative environment 600 includes a communication module 602 and a user interface module 604. Each of the modules, logic, and other components of the environment 600 may be embodied as hardware, software, firmware, or a combination thereof. For example, each of the modules, logic, and other components of the environment 600 may form a portion of, or otherwise be established by, the processor 210, the memory 214, the communication circuitry 218, and/or other hardware components of the patient computing device 108. As such, in some embodiments, one or more of the modules of the environment 600 may be embodied as circuitry or a collection of electrical devices (e.g., a communication circuit 602 and a user interface circuit 604).

The communication module 602 is configured enable the patient computing device 108 to act as a communication link between the treatment management server 102 and the smart pill 106 and physiological sensors 110. In the illustrative embodiment, the communication module 602 is configured to receive treatment data 428 from the treatment management server 102 and transmit the treatment data 428 to the smart pill 106. More specifically, in the illustrative embodiment, the communication module 602 may receive the treatment data 428 through the network 122 and transmit the treatment data 428 to the smart pill 106 using short range wireless communication (e.g., near field communication (NFC) or a Bluetooth protocol). Additionally, in the illustrative embodiment, the communication module 602 is configured to receive patient physiological data 420 from the smart pill 106 and the physiological sensors 110, and transmit the patient physiological data 420 to the treatment management server 102. In the illustrative embodiment, as described in more detail herein, the communication module 602 is configured not to transmit the patient physiological data 420 to the treatment management server 102 if the patient indicates that the patient physiological data 420 is not to be shared.

The user interface module 604 is configured to display or otherwise present information to a user, such as the patient who consumed the smart pill 106, and to receive information from the user. In the illustrative embodiment, the user interface module 604 is configured to display the patient physiological data 420 obtained by the communication module 602 from the smart pill 106 and/or the physiological sensors 110. Further, the user interface module 604 is configured to prompt the user for authorization to share the displayed patient physiological data 420 with the treatment management server 102 and to receive an authorization decision (e.g., yes or no) from the patient indicating whether the patient gives authorization for the patient physiological data 420 to be shared. Additionally, in the illustrative embodiment, the user interface module 604 is configured to prompt the patient to enter a self-reported opinion, such as a numeric rating or qualitative description of the patient's physiological status. The patient computing device 108 may add the self-reported opinion to the patient physiological data 420 to be transmitted to the treatment management server 102. It should be understood that the other patient computing devices 116 include similar modules as those described above with reference to the patient computing device 108.

Figure 7:
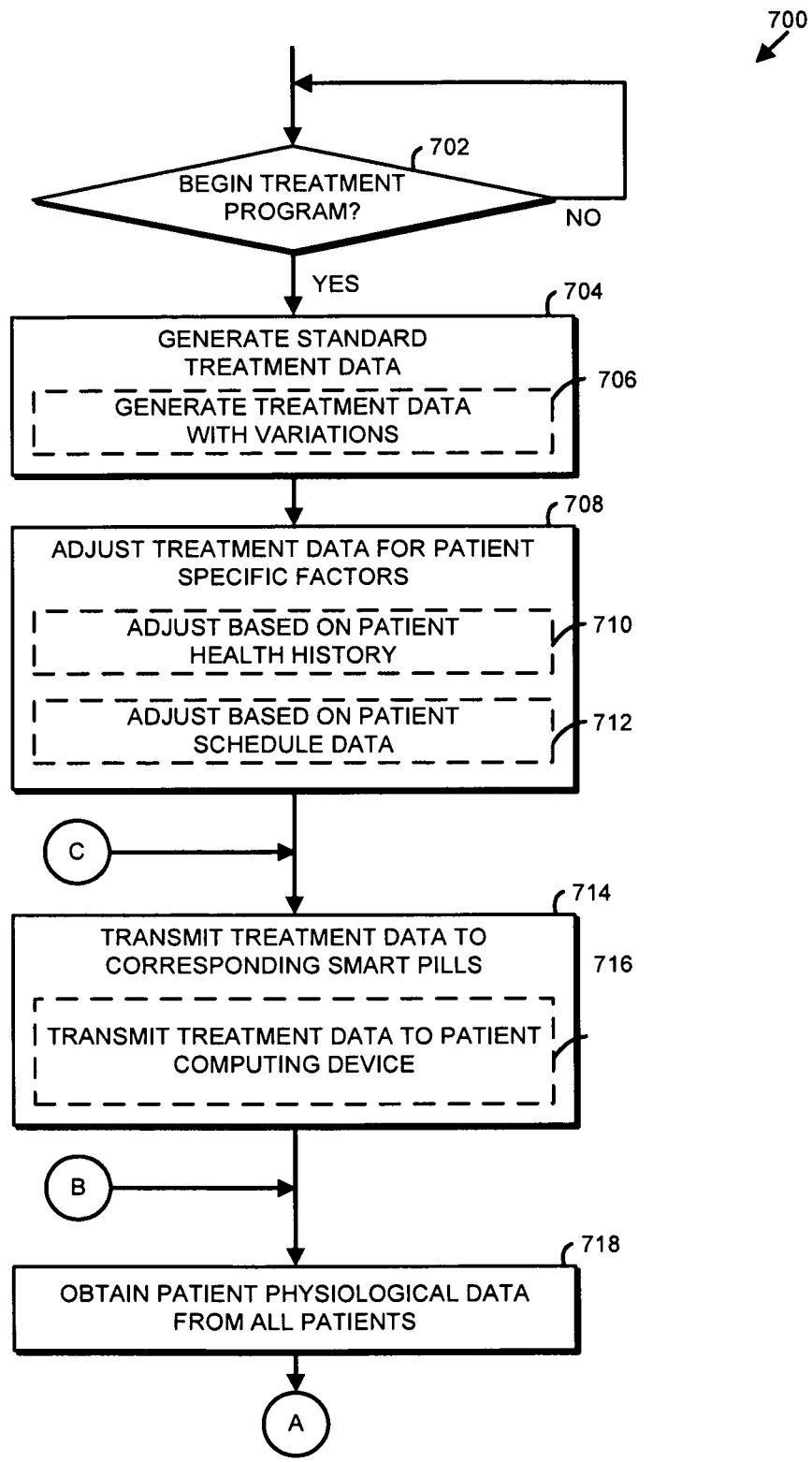
FIGS. 7-8 are a simplified flow diagram of at least one embodiment of a method for managing a treatment program that may be executed by the treatment management server of FIGS. 1 and 2.
Figure 8:
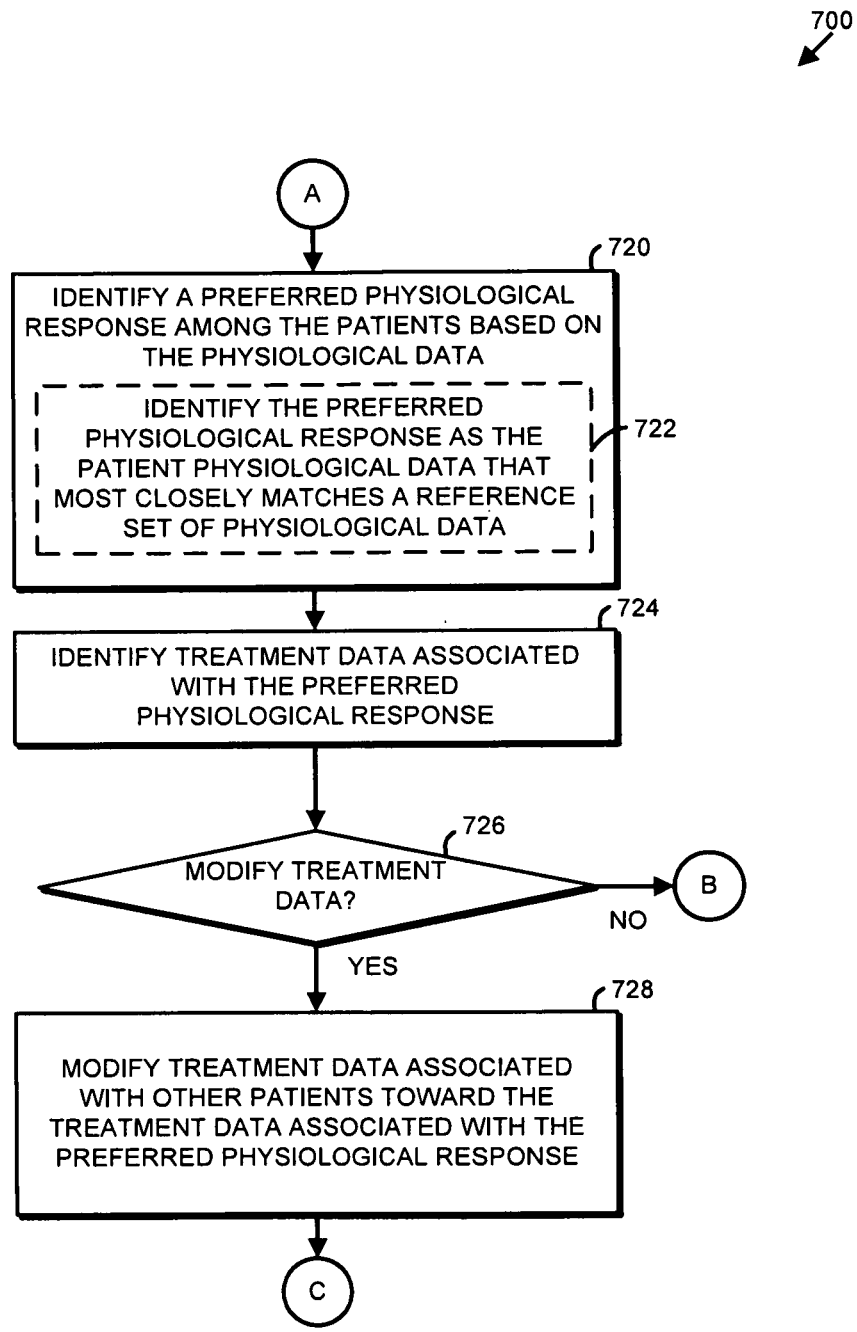

Referring now to FIGS. 7-8, in use, the treatment management server 102 may execute a method 700 for managing a treatment program. The method 700 begins with block 702, in which the treatment management server 102 determines whether to begin the treatment program. In the illustrative embodiment, the treatment management server 102 may determine that a scheduled date for the beginning of the treatment program has arrived. In other embodiments, the treatment management server 102 may receive a signal or request to begin the treatment program. In yet other embodiments, the treatment management server 102 determines to begin the treatment program based on other criteria. Regardless, after the treatment management server 102 determines to begin the treatment program, the method 700 advances to block 704. In block 704, the treatment management server 102 generates standard treatment data 428. For example, in the illustrative embodiment, the treatment management server 102 generates a single set of parameters specifying one or more drug types to be released, the amounts of the drugs to be released, and a schedule (i.e., times) for the release of the drugs, such as once every six hours. In the illustrative embodiment, in block 706, the treatment management server 102 generates the treatment data with variations. For example, the treatment management server 102 may introduce variations in the standard treatment data 428 such that one set of parameters, to be transmitted to smart pills for one patient (e.g., smart pill 106) specifies releasing 10% more of a drug than another set of parameters to be transmitted to smart pills for one or more other patient (e.g., smart pills 114). Depending on the embodiment, the treatment management server 102 may vary the drug types, the drug amounts, and/or the release schedules.

In block 708, the treatment management server 102 adjusts the treatment data 428 for patient specific factors. In the illustrative embodiment, as indicated in block 710, the treatment management server 102 may adjust the treatment data 428 based on the health history data 422. For example, the treatment management server 102 may reduce the specified amount of a particular drug in view of an indication in the health history data 422 that the patient is highly sensitive to that drug. Further, as indicated in block 712, the treatment management server 102 may adjust the treatment data 712 based on the patient's schedule data 424. For example, the schedule data 424 may indicate that the patient travels frequently and likely experiences fatigue from jet lag. Accordingly, in the example, the treatment management server 102 may increase an amount of a drug that regulates sleep.

In block 714, the treatment management server 102 transmits the treatment data 428 to the corresponding smart pills 106 and 114. The treatment management server 102 may transmit the treatment data 428 to the smart pills 106 and 114 before they are consumed or otherwise introduced into the patients' bodies or after the smart pills 106 are 114 are inside the patients' bodies (e.g., to provide an updated treatment dosage or schedule). As indicated in block 716, in the illustrative embodiment, the treatment management server 102 transmits the treatment data 428 to the corresponding patient computing devices 108 and 116 which then transmit the treatment data 428 to the corresponding smart pills 106 and 114.

In block 718, the treatment management server 102 obtains the patient physiological data 420 from all of the patients in the treatment program. In the illustrative embodiment, the treatment management server 102 receives the patient physiological data 420 from the respective patient computing devices 108 and 116. In other embodiments, the treatment management server 102 receives the patient physiological data 420 directly from the smart pills 106 and 114 and physiological sensors 110 and 118. The method 700 subsequently advances to block 720 of FIG. 8.

In block 720, the treatment management server 102 identifies a preferred physiological response among the patients, based on the physiological data 420 obtained in block 718. As indicated in block 722, in the illustrative embodiment, the treatment management server 102 identifies the preferred physiological response as the patient physiological data that most closely matches a reference set of physiological data. For example, the reference set of physiological data may indicate a blood pressure in a specific range, representing the goal of the treatment program. Accordingly, the treatment management server 102 compares each patient's physiological data 420 (i.e., their physiological responses) to the reference set of physiological data and whichever physiological response is the closest to the reference set of physiological data (e.g., the closest reported blood pressure to the blood pressure goal) is the preferred physiological response.

In block 724, the treatment management server 102 identifies the treatment data 428 associated with the preferred physiological response. For example, the treatment management server 102 may determine which smart pill 106, 114 is associated with the preferred physiological response and identify the treatment data 428 that was transmitted to that smart pill 106, 114. In block 726, the treatment management server 102 determines whether to modify the treatment data 726 based on the preferred physiological response. For example, in the illustrative embodiment, the treatment management server 102 may determine that all of the physiological responses of all of the patients are within a predefined range of the reference set of physiological data, meaning that the goal of the treatment program have been reached with the present treatment data 428 and that further modification of the treatment data 428 would not result in significant improvements. In such a scenario, the treatment management server 102 determines not to modify the treatment data 428, and the method 700 advances to block 718 of FIG. 7 in which the treatment management server 102 again obtains patient physiological data from all of the patients. In other words, the treatment data 428 stays the same as it was and the treatment management server 102 continues to monitor the physiological data 420 associated with the patients in the treatment program.

If, in block 726, the treatment management server 102 instead determines to modify the treatment data 428, the method advances to block 728, in which the treatment management server 102 modifies the treatment data associated with the other patients (i.e., the patients who did not have the preferred physiological response) toward the treatment data 428 associated with the preferred physiological response. For example, the treatment management server 102 may determine that the smart pills 106, 114 for the patients who did not have the preferred physiological response received treatment data 428 that specified a lower amount of a particular drug than the treatment data 428 associated with the preferred physiological response. Accordingly, in the example, the treatment management server 102 may increase the amount of the drug in the treatment data 428 to be transmitted to the smart pills of the patients who did not experience the preferred physiological response. The method 700 then loops back to block 714 of FIG. 7, in which the treatment management server 102 transmits the modified treatment data 428 to the corresponding smart pills 106, 114 to update the patient's treatment.

Some embodiments of the treatment management server 102 may be used in a study of treatment effects, such as a randomized drug trial. With patient consent, a randomly assigned group within a population may receive the same smart pills as the rest of the population, but the treatment management server 102 may be configured to cause a different drug, a different amount of a drug, or no drug to be dispensed from the smart pills of a randomly assigned group.

Figure 9:
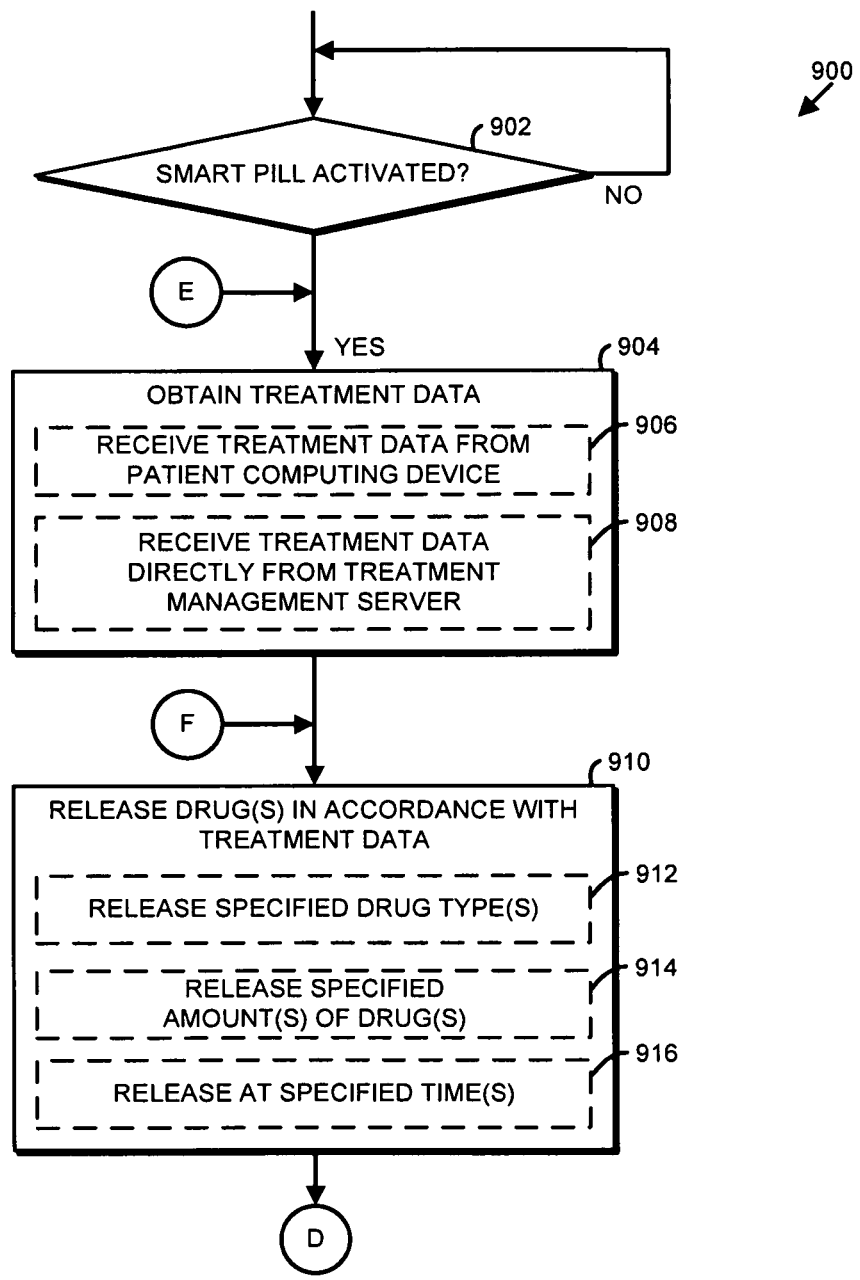
FIGS. 9-10 are a simplified flow diagram of at least one embodiment of a method for releasing drugs in a patient and reporting patient physiological data that may be performed by a smart pill of FIGS. 1 and 3.
Figure 10:
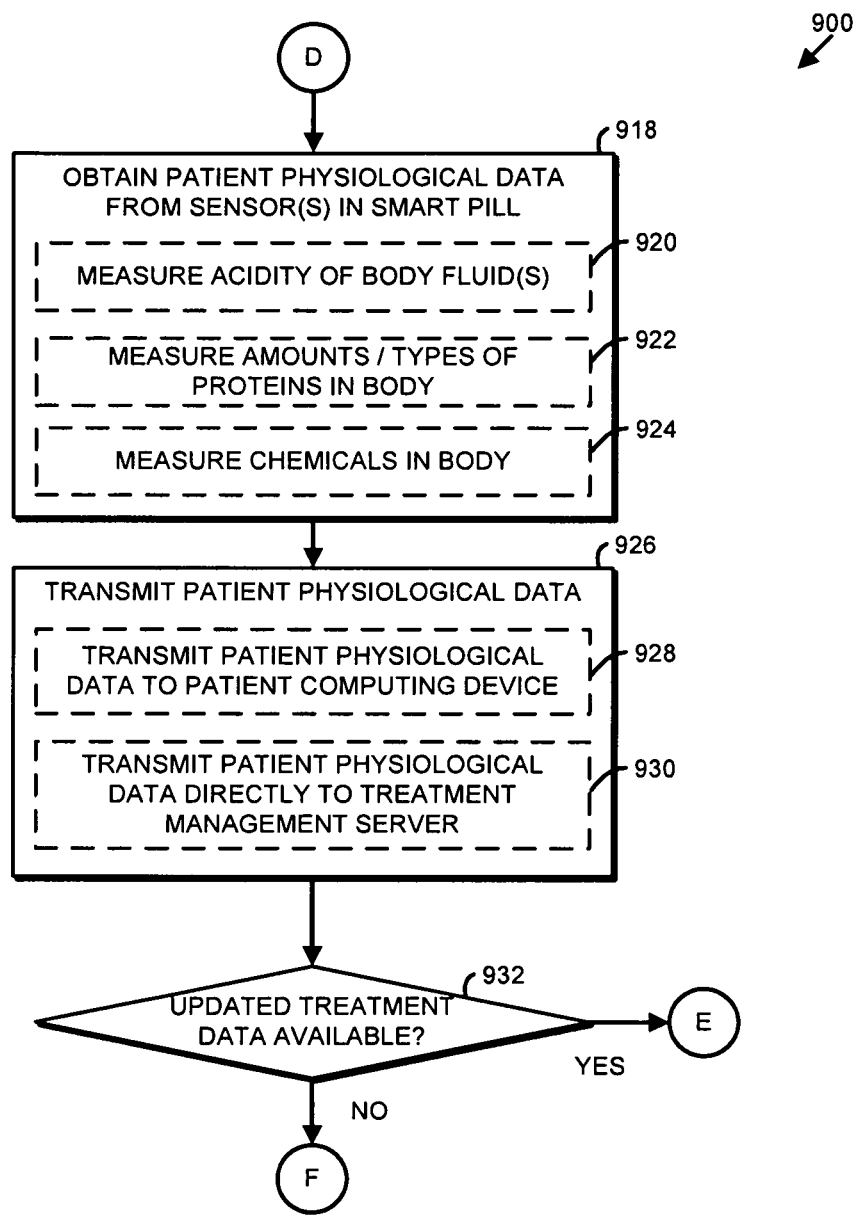

The treatment management server 102 may then compare physiological data 420 statistics across the groups to make determinations about treatment effects in the population Referring now to FIGS. 9-10, in use, each smart pill 106, 114 may execute a method 900 for releasing drugs and reporting patient physiological data. The method 900 begins with block 902, in which the smart pill 106, 114 waits until it is activated or otherwise triggered to begin operations. Once the smart pill 106, 114 is activated, or otherwise triggered, the method 900 advances to block 904 in which the smart pill 106, 114 obtains the treatment data 428. In the illustrative embodiment, as indicated in block 906, the smart pill 106, 114 receives the treatment data 428 from the corresponding patient computing device 108. For example, the smart pill 106, 114 may receive the treatment data 428 from the patient computing device 108 through short range wireless communication. In other embodiments, as indicated in block 908, the smart pill 106, 114 may receive the treatment data 428 directly from the treatment management server 102. Regardless, in block 910, the smart pill 106, 114 releases one or more of the drugs 334 and 336 in the body of the patient in accordance with the treatment data 428. For example, as indicated in block 912, the smart pill 106, 114 may release one or more drugs of one or more types specified in the treatment data 428. Further, as indicated in block 914, the smart pill 106, 114 may release particular amounts of the one or more drugs as specified in the treatment data 428. Additionally, as indicated in block 916, the smart pill 106, 114 may release the one or more drugs at one or more times specified in the treatment data 428. After the smart pill 106, 114 has released the drug(s) according to the treatment data, the method 900 advances to block 918 of FIG. 10.

In block 918, the smart pill 106, 114 obtains the patient physiological data 420 from one or more of the sensors 330. For example, as indicated in block 920, the smart pill 106, 114 may measure an acidity of one or more body fluids in the patient. As another example, as indicated in block 922, the smart pill 106, 114 may measure amounts and/or types of proteins in the patient's body. As yet another example, as indicated in block 924, the smart pill 106, 114 may measure one or more chemicals in the patient's body 924.

In block 926, the smart pill 106, 114 transmits the patient physiological data 420. In the illustrative embodiment, as indicated in block 928, the smart pill 106 transmits the patient physiological data 420 to the corresponding patient computing device 108. In the illustrative embodiment, the patient computing device 108 subsequently transmits the physiological data 420 to the treatment management server 102. However, in other embodiments as indicated in block 930, the smart pill 106, 114 may transmit the patient physiological data directly to the treatment management server 102. Regardless, in block 932, the smart pill 106, 114 determines whether updated treatment data 428 is available. For example, the smart pill 106, 114 may query the patient computing device 108 or the treatment management server 102, for updated treatment data 428 to determine whether updated treatment data is available. In other embodiments, the smart pill 106, 114 may detect that the patient computing device 108 or the treatment management server 102 is attempting to transmit updated treatment data 428 to it, without affirmatively querying for the updated treatment data 428. Regardless, if updated treatment data is available, the method 900 advances to block 904 of FIG. 9, and the smart pill 106 obtains the updated treatment data 428. Otherwise, the method 900 advances to block 910 of FIG. 9, and the smart pill 106 continues release of the one or more of the drugs 334 and 336 in accordance with the existing treatment data 428.

Figure 11:
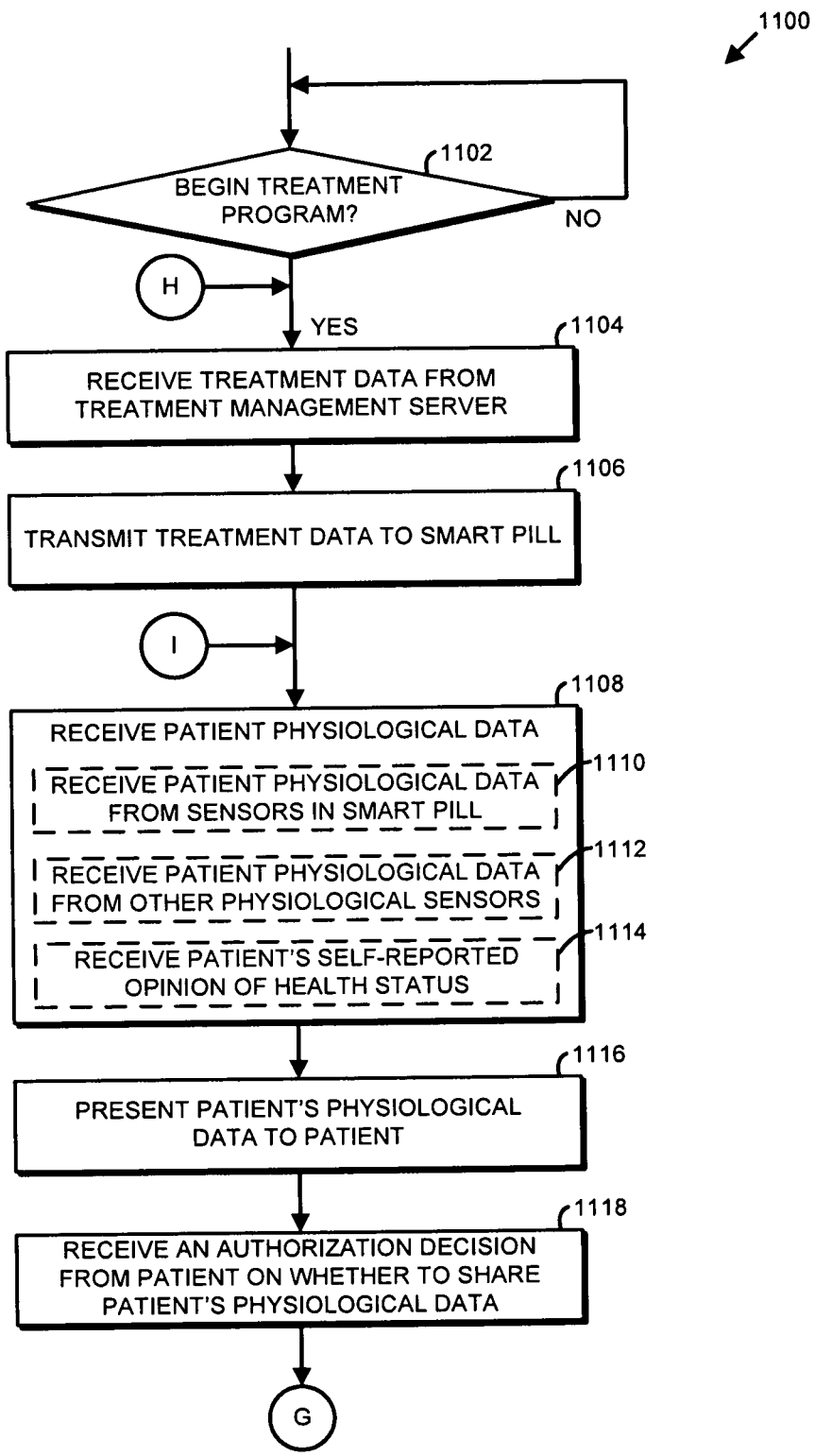
FIGS. 11-12 are a simplified flow diagram of at least one embodiment of a method for communicating with the treatment management server and a smart pill that may be performed by a patient computing device of FIG. 1.
Figure 12:
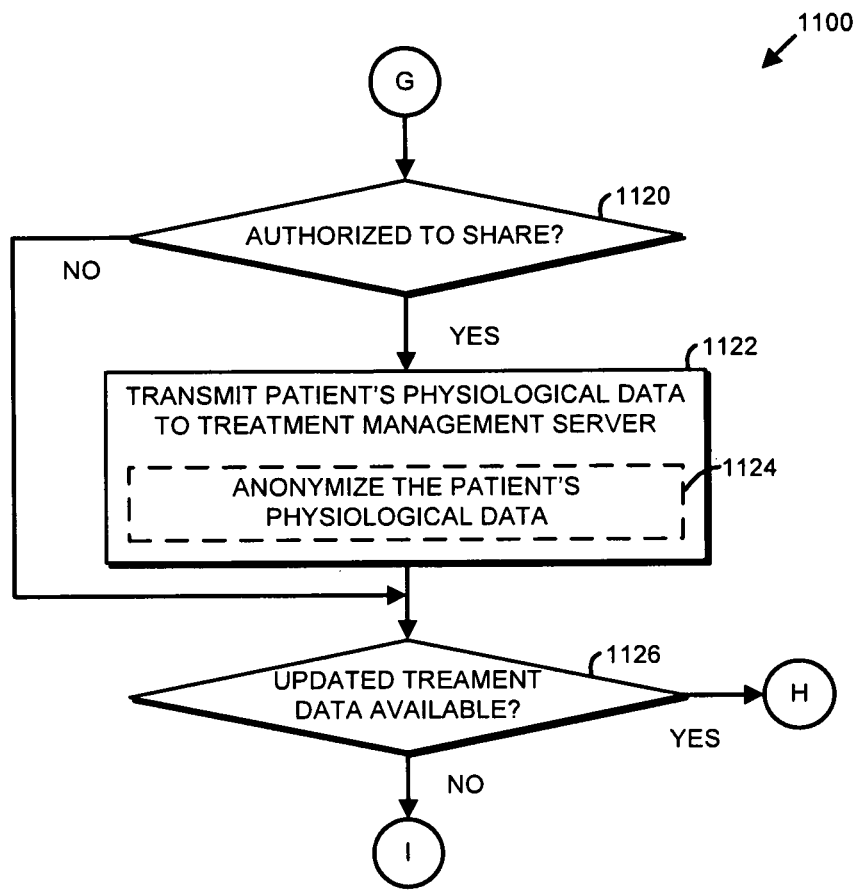

Referring now to FIGS. 11-12, in use, each patient computing device 108, 116 may execute a method 1100 for communicating with the treatment management server 102 and the smart pill 106. The method 1100 begins with block 1102, in which the patient computing device 102 determines whether to begin the treatment program. In the illustrative embodiment, the patient computing device 108, 116 may determine that a scheduled date for the beginning of the treatment program has arrived. In other embodiments, the patient computing device 108, 116 may receive a signal or request to begin the treatment program. In yet other embodiments, the patient computing device 108, 116 may determine to begin the treatment program based on other criteria. Regardless, after the patient computing device 108, 116 determines to begin the treatment program, the method 1100 advances to block 1104.

In block 1104, the patient computing device 108, 116 receives the treatment data 428 from the treatment management server 102. In the illustrative embodiment, the patient computing device 108, 116 receives the treatment data 428 via the network 122. In block 1106, the patient computing device 108, 116 transmits the treatment data 428 to the corresponding smart pill 106. In some embodiments, the patient computing device 108, 116 may transmit the treatment data 428 to the smart pill 106 before the smart pill 106 is inside the patient's body. In other embodiments, the patient computing device 108, 116 may transmit the treatment data 428 to the smart pill 106 after the smart pill 106 is inside the patient's body. In the illustrative embodiment, the patient computing device 106 transmits the treatment data 428 to the smart pill 108 using short range wireless communication, such as NFC or a Bluetooth protocol.

In block 1108, the patient computing device 108, 116 receives the patient physiological data 420. In the illustrative embodiment, in block 1110, the patient computing device 108, 116 may receive the patient physiological data 420 generated by one or more of the sensors 330 in the smart pill 106. Further, as indicated in block 1112, the patient computing device 108, 116 may receive additional patient physiological data 420 from the physiological sensors 110 (e.g., heart rates, blood pressures, brain activity levels, body temperatures, bacteria levels, virus levels, etc.). Further, as indicated in block 1114, the patient computing device 108, 116 may receive additional patient physiological data 420 as the patient's self-reported opinion of the patient's health status. For example, the patient computing device 108, 116 may prompt the patient to enter a ranking, description, or other indication of the how the patient is feeling, and may receive the self-reported opinion in response to the prompt.

In block 1116, the patient computing device 108, 116 presents the patient's physiological data 420 to the patient. For example, the patient computing device 108, 116 may display the physiological data 420 to the patient. In block 1118, the patient computing device 108, 116 receives an authorization decision from the patient on whether to share the patient's physiological data 420. For example, the patient computing device 108, 116 may prompt the patient for authorization to share the physiological data and receive an authorization decision from the patient in response to the prompt. After the patient computing device 108, 116 receives the authorization decision from the patient in block 1118, the method 1100 advances to block 1120 of FIG. 12.

In block 1120, the patient computing device 1120 determines whether the patient has provided authorization to share the patient's physiological data 420. If the patient has provided authorization to share the patient's physiological data 420, the method 1100 advances to block 1122. In block 1122, the patient computing device 108, 116 transmits the patient's physiological data 420 to the treatment management server 102. In the illustrative embodiment, in block 1124, the patient computing device 108, 116 anonymizes the physiological data 420. For example, the patient computing device 108, 116 may remove any personally identifying information from the patient's physiological data 420 before transmitting the patient's physiological data 420 to the treatment management server 102. After the patient computing device 1122 transmits the patient's physiological data in block 1122 or if the patient computing device 108, 116 determines that the patient did not provide authorization to share the patient's physiological data in block 1120, the method 1126 advances to block 1126 in which the patient computing device 108, 116 determines whether updated treatment data is available. For example, the patient computing device 108, 116 may query the treatment management server 102 to determine whether updated treatment data is available. In other embodiments, the patient computing device 108, 116 may detect that the treatment management server 102 is attempting to transmit the updated treatment data to the patient computing device 108, 116. Regardless, if updated treatment data is available, the method 1100 loops back to block 1104 of FIG. 11, wherein the patient computing device 108, 116 receives the updated treatment data from the treatment management server 102. Otherwise, the method 1100 loops back to block 1108 of FIG. 11, in which the patient computing device 108, 116 receives additional patient physiological data 420.

EXAMPLES

Illustrative examples of the technologies disclosed herein are provided below. An embodiment of the technologies may include any one or more, and any combination of, the examples described below.

Example 1 includes a treatment management server for managing treatment of patients using smart pills, the treatment management server comprising a treatment data determination module to generate treatment data usable by smart pills to control a release of one or more drugs from the smart pills and into the patients; a communication module to transmit the treatment data to the smart pills; and a data aggregator module to obtain physiological data associated with the patients, wherein the physiological data is in response to the release of the one or more drugs, wherein the treatment data determination module is further to identify a preferred physiological response among the patients based on the physiological data and identify the treatment data associated with the preferred physiological response.

Example 2 includes the subject matter of Example 1, and wherein the treatment data determination module is further to identify the preferred physiological response as the patient physiological data that most closely matches a reference set of physiological data.

Example 3 includes the subject matter of any of Examples 1 and 2, and wherein the treatment data determination module is further to determine whether to modify the treatment data in response to the identification of the preferred response and modify the treatment data associated with the patients toward the identified treatment data associated with the preferred physiological response, in response to a determination to modify the treatment data; and the communication module is further to transmit the modified treatment data to the smart pills.

Example 4 includes the subject matter of any of Examples 1-3, and wherein the treatment data determination module is further to adjust the treatment data based on one or more patient specific factors before the communication module transmits the treatment data to the smart pills.

Example 5 includes the subject matter of any of Examples 1-4, and wherein to adjust the treatment data based on one or more patient specific factors comprises to adjust the treatment data based on patient health history data.

Example 6 includes the subject matter of any of Examples 1-5, and wherein to adjust the treatment data based on one or more patient specific factors comprises to adjust the treatment data based on patient schedule data.

Example 7 includes the subject matter of any of Examples 1-6, and wherein the treatment data determination module is further to apply one or more heuristics to the patient specific factors to adjust the treatment data.

Example 8 includes the subject matter of any of Examples 1-7, and wherein the treatment data determination module is further to vary the treatment data associated with each of the smart pills before the treatment data is transmitted to the smart pills.

Example 9 includes the subject matter of any of Examples 1-8, and wherein to transmit the treatment data to the smart pills comprises to transmit the treatment data to one or more patient computing devices configured to transmit the treatment data to the smart pills.

Example 10 includes the subject matter of any of Examples 1-9, and wherein to obtain the patient physiological data comprises to obtain patient physiological data generated by sensors in the smart pills.

Example 11 includes the subject matter of any of Examples 1-10, and wherein to obtain the patient physiological data comprises to obtain physiological data from at least one of a wearable sensor, a body fluid sensor, an environmental sensor, and a patient computing device.

Example 12 includes the subject matter of any of Examples 1-11, and wherein to obtain the patient physiological data comprises to obtain a patient-reported health status opinion.

Example 13 includes the subject matter of any of Examples 1-12, and wherein to obtain the patient physiological data comprises to obtain anonymized patient physiological data.

Example 14 includes the subject matter of any of Examples 1-13, and wherein to generate the treatment data comprises to generate treatment data that specifies at least one of a drug type, a drug release amount, and a drug release schedule.

Example 15 includes a method for managing treatment of patients using smart pills, the method comprising generating, by a treatment management server, treatment data usable by smart pills to control a release of one or more drugs from the smart pills and into the patients; transmitting, by the treatment management server, the treatment data to the smart pills; obtaining, by the treatment management server, physiological data associated with the patients, wherein the physiological data is in response to the release of the one or more drugs; identifying, by the treatment management server, a preferred physiological response among the patients based on the physiological data; and identifying, by the treatment management server, the treatment data associated with the preferred physiological response.

Example 16 includes the subject matter of Example 15, and further including identifying, by the treatment management server, the preferred physiological response as the patient physiological data that most closely matches a reference set of physiological data.

Example 17 includes the subject matter of any of Examples 15 and 16, and further including determining, by the treatment management server, whether to modify the treatment data in response to the identification of the preferred response; modifying, by the treatment management server, the treatment data associated with the patients towards the identified treatment data associated with the preferred physiological response, in response to a determination to modify the treatment data; and transmitting, by the treatment management server, the modified treatment data to the smart pills.

Example 18 includes the subject matter of any of Examples 15-17, and further including adjusting the treatment data based on one or more patient specific factors before transmitting the treatment data to the smart pills.

Example 19 includes the subject matter of any of Examples 15-18, and wherein adjusting the treatment data comprises adjusting the treatment data based on patient health history data.

Example 20 includes the subject matter of any of Examples 15-19, and wherein adjusting the treatment data comprises adjusting the treatment data based on patient schedule data.

Example 21 includes the subject matter of any of Examples 15-20, and wherein adjusting the treatment data comprises applying one or more heuristics to the patient specific factors.

Example 22 includes the subject matter of any of Examples 15-21, and further including varying, by the treatment management server, the treatment data associated with each of the smart pills before transmitting the treatment data to the smart pills.

Example 23 includes the subject matter of any of Examples 15-22, and wherein transmitting the treatment data to the smart pills comprises transmitting the treatment data to one or more patient computing devices configured to transmit the treatment data to the smart pills.

Example 24 includes the subject matter of any of Examples 15-23, and wherein obtaining the patient physiological data comprises obtaining patient physiological data generated by sensors in the smart pills.

Example 25 includes the subject matter of any of Examples 15-24, and wherein obtaining the patient physiological data comprises obtaining physiological data from at least one of a wearable sensor, a body fluid sensor, an environmental sensor, and a patient computing device.

Example 26 includes the subject matter of any of Examples 15-25, and wherein obtaining the patient physiological data comprises obtaining a patient-reported health status opinion.

Example 27 includes the subject matter of any of Examples 15-26, and wherein obtaining the patient physiological data comprises obtaining anonymized patient physiological data.

Example 28 includes the subject matter of any of Examples 15-27, and wherein generating the treatment data comprises generating treatment data that specifies at least one of a drug type, a drug release amount, and a drug release schedule.

Example 29 includes one or more computer-readable storage media comprising a plurality of instructions that, when executed, cause a treatment management server to perform the method of any of Examples 15-28.

Example 30 includes a treatment management server for managing treatment of patients using smart pills, the treatment management server comprising means for generating treatment data usable by smart pills to control a release of one or more drugs from the smart pills and into the patients; means for transmitting the treatment data to the smart pills; means for obtaining physiological data associated with the patients, wherein the physiological data is in response to the release of the one or more drugs; means for identifying a preferred physiological response among the patients based on the physiological data; and means for identifying the treatment data associated with the preferred physiological response.

Example 31 includes the subject matter of Example 30, further including means for identifying the preferred physiological response as the patient physiological data that most closely matches a reference set of physiological data.

Example 32 includes the subject matter of any of Examples 30 and 31, further including means for determining whether to modify the treatment data in response to the identification of the preferred response; means for modifying the treatment data associated with the patients towards the identified treatment data associated with the preferred physiological response, in response to a determination to modify the treatment data; and means for transmitting the modified treatment data to the smart pills.

Example 33 includes the subject matter of any of Examples 30-32, and further including means for adjusting the treatment data based on one or more patient specific factors before transmitting the treatment data to the smart pills.

Example 34 includes the subject matter of any of Examples 30-33, and wherein the means for adjusting the treatment data comprises means for adjusting the treatment data based on patient health history data.

Example 35 includes the subject matter of any of Examples 30-34, and wherein the means for adjusting the treatment data comprises means for adjusting the treatment data based on patient schedule data.

Example 36 includes the subject matter of any of Examples 30-35, and wherein the means for adjusting the treatment data comprises means for applying one or more heuristics to the patient specific factors.

Example 37 includes the subject matter of any of Examples 30-36, and further including means for varying the treatment data associated with each of the smart pills before transmitting the treatment data to the smart pills.

Example 38 includes the subject matter of any of Examples 30-37, and wherein the means for transmitting the treatment data to the smart pills comprises means for transmitting the treatment data to one or more patient computing devices configured to transmit the treatment data to the smart pills.

Example 39 includes the subject matter of any of Examples 30-38, and wherein the means for obtaining the patient physiological data comprises means for obtaining patient physiological data generated by sensors in the smart pills.

Example 40 includes the subject matter of any of Examples 30-39, and wherein the means for obtaining the patient physiological data comprises means for obtaining physiological data from at least one of a wearable sensor, a body fluid sensor, an environmental sensor, and a patient computing device.

Example 41 includes the subject matter of any of Examples 30-40, and wherein the means for obtaining the patient physiological data comprises means for obtaining a patient-reported health status opinion.

Example 42 includes the subject matter of any of Examples 30-41, and wherein the means for obtaining the patient physiological data comprises means for obtaining anonymized patient physiological data.

Example 43 includes the subject matter of any of Examples 30-42, and wherein the means for generating the treatment data comprises means for generating treatment data that specifies at least one of a drug type, a drug release amount, and a drug release schedule.

Example 44 includes a smart pill for controlling drug release in a patient, the smart pill comprising one or more drug reservoirs containing a drug to be administered to the patient; one or more drug release mechanisms, wherein each drug release mechanism is operatively coupled to a corresponding one of the one or more drug reservoirs to control the release of the drug from the corresponding drug reservoir and into the patient; a communication module to obtain treatment data from a computing device; and a drug release controller module to control the drug release mechanisms to release one or more drugs into the patient in accordance with the treatment data, after the smart pill has been consumed by the patient; and at least one sensor to sense patient physiological data associated with the patient, wherein the patient physiological data is in response to the release of the one or more drugs, wherein the communication module is further to transmit the patient physiological data to the computing device.

Example 45 the subject matter of Example 44, and wherein to obtain the treatment data comprises to obtain the treatment data from a patient computing device that received the treatment data from a treatment management server.

Example 46 includes the subject matter of any of Examples 44 and 45, and wherein to obtain the treatment data comprises to obtain the treatment data from a treatment management server that generated the treatment data.

Example 47 includes the subject matter of any of Examples 44-46, and wherein to release one or more drugs comprises to release one or more drugs in accordance with one or more drug types specified in the treatment data.

Example 48 includes the subject matter of any of Examples 44-47, and wherein to release one or more drugs comprises to release one or more drug amounts specified in the treatment data.

Example 49 includes the subject matter of any of Examples 44-48, and wherein to release one or more drugs comprises to release one or more drugs at one or more times specified in the treatment data.

Example 50 includes the subject matter of any of Examples 44-49, and wherein to generate the patient physiological data comprises to measure an acidity of one or more body fluids in the patient.

Example 51 includes the subject matter of any of Examples 44-50, and wherein to generate the patient physiological data comprises to measure proteins in the patient.

Example 52 includes the subject matter of any of Examples 44-51, and wherein to generate the patient physiological data comprises to measure one or more chemicals in the patient.

Example 53 includes the subject matter of any of Examples 44-52, and wherein the communication module is further to receive updated treatment data that was modified based on the transmitted patient physiological data; and the drug release controller module is further to release the one or more drugs in accordance with the updated treatment data.

Example 54 includes a method for controlling drug release in a patient, the method comprising obtaining, by a smart pill, treatment data from a computing device; releasing, by the smart pill, one or more drugs into the patient in accordance with the treatment data, after the smart pill has been consumed by the patient; generating, by the smart pill, patient physiological data associated with the patient, wherein the patient physiological data is in response to releasing the one or more drugs into the patient; and transmitting, by the smart pill, the patient physiological data to the computing device.

Example 55 includes the subject matter of Example 54, and wherein obtaining the treatment data comprises obtaining the treatment data from a patient computing device that received the treatment data from a treatment management server.

Example 56 includes the subject matter of any of Examples 54 and 55, and wherein obtaining the treatment data comprises obtaining the treatment data from a treatment management server that generated the treatment data.

Example 57 includes the subject matter of any of Examples 54-56, and wherein releasing one or more drugs comprises releasing one or more drugs according to one or more drug types specified in the treatment data.

Example 58 includes the subject matter of any of Examples 54-57, and wherein releasing one or more drugs comprises releasing one or more drug amounts specified in the treatment data.

Example 59 includes the subject matter of any of Examples 54-58, and wherein releasing one or more drugs comprises releasing one or more drugs at one or more times specified in the treatment data.

Example 60 includes the subject matter of any of Examples 54-59, and wherein generating the patient physiological data comprises measuring an acidity of one or more body fluids in the patient.

Example 61 includes the subject matter of any of Examples 54-60, and wherein generating the patient physiological data comprises measuring proteins in the patient.

Example 62 includes the subject matter of any of Examples 54-61, and wherein generating the patient physiological data comprises measuring one or more chemicals in the patient.

Example 63 includes the subject matter of any of Examples 54-62, and further including receiving, by the smart pill, updated treatment data that was modified based on the transmitted patient physiological data; and releasing, by the smart pill, the one or more drugs in accordance with the updated treatment data.

Example 64 includes one or more computer-readable storage media comprising a plurality of instructions that, when executed, cause a smart pill to perform the method of any of Examples 54-63.

Example 65 includes a smart pill for controlling drug release in a patient, the smart pill comprising means for obtaining treatment data from a computing device means for releasing one or more drugs into the patient in accordance with the treatment data, after the smart pill has been consumed by the patient means for generating patient physiological data associated with the patient, wherein the patient physiological data is in response to releasing the one or more drugs into the patient; and means for transmitting the patient physiological data to the computing device.

Example 66 includes the subject matter of Example 65, and wherein the means for obtaining the treatment data comprises means for obtaining the treatment data from a patient computing device that received the treatment data from a treatment management server.

Example 67 includes the subject matter of any of Examples 65 and 66, and wherein the means for obtaining the treatment data comprises means for obtaining the treatment data from a treatment management server that generated the treatment data.

Example 68 includes the subject matter of any of Examples 65-67, and wherein the means for releasing one or more drugs comprises means for releasing one or more drugs according to one or more drug types specified in the treatment data.

Example 69 includes the subject matter of any of Examples 65-68, and wherein the means for releasing one or more drugs comprises means for releasing one or more drug amounts specified in the treatment data.

Example 70 includes the subject matter of any of Examples 65-69, and wherein the means for releasing one or more drugs comprises means for releasing one or more drugs at one or more times specified in the treatment data.

Example 71 includes the subject matter of any of Examples 65-70, and wherein the means for generating the patient physiological data comprises means for measuring an acidity of one or more body fluids in the patient.

Example 72 includes the subject matter of any of Examples 65-71, and wherein the means for generating the patient physiological data comprises means for measuring proteins in the patient.

Example 73 includes the subject matter of any of Examples 65-72, and wherein the means for generating the patient physiological data comprises means for measuring one or more chemicals in the patient.

Example 74 includes the subject matter of any of Examples 65-73, and further including means for receiving updated treatment data that was modified based on the transmitted patient physiological data; and means for releasing the one or more drugs in accordance with the updated treatment data.

Example 75 includes a patient computing device for communicating with a treatment management server and a smart pill, the patient computing device comprising a communication module to (i) receive treatment data from the treatment management server, wherein the treatment data is usable by the smart pill to control a release of one or more drugs into a patient, (ii) transmit the treatment data to the smart pill, and (iii) receive patient physiological data from the smart pill, wherein the patient physiological data is in response to the release of the one or more drugs into the patient; and a user interface module to present the received patient physiological data to the patient.

Example 76 includes the subject matter of Example 75, and wherein the user interface module is further to prompt the patient for authorization to share the patient physiological data and receive an authorization decision from the patient to share the patient physiological data; and the communication module is further to transmit the patient physiological data to the treatment management server in response to an authorization decision that provides authorization to share the patient physiological data.

Example 77 includes the subject matter of any of Examples 75 and 76, and wherein the patient communication module is further to anonymize the patient physiological data; and transmit the patient physiological data to the treatment management server.

Example 78 includes the subject matter of any of Examples 75-77, and wherein the communication module is further to receive the patient physiological data from at least one of a wearable sensor, a body fluid sensor, and an environmental sensor associated with the patient.

Example 79 includes the subject matter of any of Examples 75-78, and wherein the user interface is further to prompt the patient for a self-reported opinion of a health status of the patient and receive the self-reported opinion in response to the prompt; and the communication module is further to transmit the self-reported opinion of the health status to the treatment management server.

Example 80 includes the subject matter of any of Examples 75-79, and wherein the communication module is further to determine whether updated treatment data is available from the treatment management server; receive the updated treatment data from the treatment management server in response to a determination that the updated treatment data is available; and transmit the updated treatment data to the smart pill.

Example 81 includes a method for communicating with a treatment management server and a smart pill using a patient computing device, the method comprising receiving, by the patient computing device, treatment data from the treatment management server, wherein the treatment data is usable by the smart pill to control a release of one or more drugs into a patient; transmitting, by the patient computing device, the treatment data to the smart pill; receiving, by the patient computing device, patient physiological data from the smart pill, wherein the patient physiological data is in response to the release of the one or more drugs into the patient; and presenting, by the patient computing device, the received patient physiological data to the patient.

Example 82 includes the subject matter of Example 81, and further including prompting, by the patient computing device, the patient for authorization to share the patient physiological data; receiving, by the patient computing device, an authorization decision from the patient to share the patient physiological data; and transmitting, by the patient computing device, the patient physiological data to the treatment management server in response to an authorization decision that provides authorization to share the patient physiological data.

Example 83 includes the subject matter of any of Examples 81 and 82, and further including anonymizing, by the patient computing device, the patient physiological data; and transmitting, by the patient computing device, the patient physiological data to the treatment management server.

Example 84 includes the subject matter of any of Examples 81-83, and further including receiving, by the patient computing device, additional patient physiological data from at least one of a wearable sensor, a body fluid sensor, and an environmental sensor associated with the patient.

Example 85 includes the subject matter of any of Examples 81-84, and further including prompting, by the patient computing device, the patient for a self-reported opinion of a health status of the patient; receiving, by the patient computing device, the self-reported opinion in response to the prompt; and transmitting, by the patient computing device, the self-reported opinion of the health status to the treatment management server.

Example 86 includes the subject matter of any of Examples 81-85, and further including determining, by the patient computing device, whether updated treatment data is available from the treatment management server; receiving, by the patient computing device, the updated treatment data from the treatment management server in response to a determination that the updated treatment data is available; and transmitting, by the patient computing device, the updated treatment data to the smart pill.

Example 87 includes one or more computer-readable storage media comprising a plurality of instructions that, when executed, cause a patient computing device to perform the method of any of Examples 81-86.

Example 88 includes a patient computing device for communicating with a treatment management server and a smart pill, the patient computing device comprising means for receiving treatment data from the treatment management server, wherein the treatment data is usable by the smart pill to control a release of one or more drugs into a patient; means for transmitting the treatment data to the smart pill; means for receiving patient physiological data from the smart pill, wherein the patient physiological data is in response to the release of the one or more drugs into the patient; and means for presenting the received patient physiological data to the patient.

Example 89 includes the subject matter of Example 88, and further including means for prompting the patient for authorization to share the patient physiological data; means for receiving an authorization decision from the patient to share the patient physiological data; and means for transmitting the patient physiological data to the treatment management server in response to an authorization decision that provides authorization to share the patient physiological data.

Example 90 includes the subject matter of any of Examples 88 and 89, and further including means for anonymizing the patient physiological data; and means for transmitting the patient physiological data to the treatment management server.

Example 91 includes the subject matter of any of Examples 88-90, and further including means for receiving additional patient physiological data from at least one of a wearable sensor, a body fluid sensor, and an environmental sensor associated with the patient.

Example 92 includes the subject matter of any of Examples 88-91, and further including means for prompting the patient for a self-reported opinion of a health status of the patient; means for receiving the self-reported opinion in response to the prompt; and means for transmitting the self-reported opinion of the health status to the treatment management server.

Example 93 includes the subject matter of any of Examples 88-92, and further comprising means for determining whether updated treatment data is available from the treatment management server; means for receiving the updated treatment data from the treatment management server in response to a determination that the updated treatment data is available; and means for transmitting the updated treatment data to the smart pill.

The invention claimed is:

1. A system to manage treatment of patients using smart pills, the system comprising:
   memory; and
   one or more processors to:
      generate first treatment data usable by a first smart pill and second treatment data usable by a second smart pill, the first smart pill to control a release of a first drug from the first smart pill in a first patient, the second smart pill to control the release of the first drug from the second smart pill in a second patient;
      transmit the first treatment data to the first smart pill and the second treatment data to the second smart pill;
      obtain, from the first smart pill, first physiological data associated with the first patient, wherein the first physiological data is in response to the release of the first drug from the first smart pill;
      obtain, from the second smart pill, second physiological data associated with the second patient, wherein the second physiological data is in response to the release of the first drug from the second smart pill;
      perform a first comparison of the first physiological data to third physiological data, the third physiological data being reference physiological data;
      perform a second comparison of the second physiological data to the third physiological data;
      identify the first patient or the second patient as having a target physiological response based on the first comparison and the second comparison;
      modify the first treatment data or the second treatment data associated with which of the first patient or the second patient did not have the target physiological response; and
      transmit the modified first treatment data or the modified second treatment data to the respective first smart pill or the second smart pill to cause release of at least one of a second drug or a different amount of the first drug.

2. The system of claim 1, wherein the one or more processors are to adjust at least one of the first treatment data or the second treatment data based on one or more patient specific factors before the one or more processors transmit at least one of the first treatment data to the first smart pill or the second treatment data to the second smart pill.

3. The system of claim 2, wherein the patient specific factors include patient health history data.

4. The system of claim 2, wherein the patient specific factors include patient schedule data.

5. The system of claim 2, wherein the one or more processors are to apply one or more heuristics to the patient specific factors to adjust at least one of the first treatment data or the second treatment data.

6. The system of claim 1, wherein the second treatment data is different than the first treatment data.

7. The system of claim 1, wherein to transmit the first treatment data to the first smart pill and the second treatment data to the second smart pill, the one or more processors are to transmit the first and second treatment data to one or more patient computing devices that are to transmit the first treatment data and the second treatment data to the respective first and second smart pills.

8. The system of claim 1, wherein the one or more processors are to transmit the first treatment data to the first smart pill and the second treatment data to the second smart pill after the first and second smart pills are consumed by the respective first and second patients.

9. The system of claim 1, wherein the one or more processors are to:
   transmit the first treatment data to the first smart pill and the second treatment data to the second smart pill before the first smart pill and second smart pill are consumed by the respective first patient and second patient; and
   transmit the modified first treatment data to the first smart pill or the modified second treatment data to the second smart pill after the first smart pill or the second smart pill is consumed by the respective first patient or second patient.

10. One or more non-transitory computer-readable storage media comprising a plurality of instructions that, when executed, cause one or more processors to:
generate first treatment data usable by a first smart pill and second treatment data usable by a second smart pill, the first smart pill to control a release of a first drug from the first smart pill in a first patient, the second smart pill to control a release of a first drug from the second smart pill in a second patient;
transmit the first treatment data to the first smart pill and the second treatment data to the second smart pill;
obtain, from the first smart pill, first physiological data associated with the first patient, wherein the first physiological data is in response to the release of the first drug from the first smart pill;
obtain, from the second smart pill, second physiological data associated with the second patient, wherein the second physiological data is in response to the release of the first drug from the second smart pill;
perform a first comparison of the first physiological data to third physiological data, the third physiological data being reference physiological data;
perform a second comparison of the second physiological data to the third physiological data;
identify the first patient or the second patient as having a target physiological response based on the first comparison and the second comparison;
modify the first treatment data or the second treatment data associated with which of the first patient or the second patient did not have the target physiological response; and
transmit the modified first treatment data or the modified second treatment data to the respective first smart pill or the second smart pill to cause release of at least one of a second drug or a different amount of the first drug.

11. The one or more non-transitory computer-readable storage media of claim 10, wherein the instructions cause the one or more processors to adjust at least one of the first treatment data or the second treatment data based on one or more patient specific factors before causing the one or more processors to transmit at least one of the first treatment data to the first smart pill or the second treatment data to the second smart pill.

12. The one or more non-transitory computer-readable storage media of claim 11, wherein the patient specific factors include patient health history data.

13. The one or more non-transitory computer-readable storage media of claim 11, wherein the patient specific factors include patient schedule data.

14. The one or more non-transitory computer-readable storage media of claim 11, wherein the instructions cause the one or more processors to apply one or more heuristics to the patient specific factors to adjust at least one of the first treatment data or the second treatment data.

15. The one or more non-transitory computer-readable storage media of claim 11, wherein to transit the first treatment data to the first smart pill and the second treatment data to the second smart pill, the instructions cause the one or more processors to transmit the first and second treatment data to one or more patient computing devices that are to transmit the first treatment data and the second treatment data to the respective first and second smart pills.

16. The one or more non-transitory computer-readable storage media of claim 10, wherein the second treatment data is different than the first treatment data.

17. The one or more non-transitory computer-readable storage media of claim 10, further including a plurality of instructions that, when executed, cause the one or more processors to transmit the first treatment data to the first smart pill and the second treatment data to the second smart pill after the first and second smart pills are consumed by the first and second patient.

18. The one or more non-transitory computer-readable storage media of claim 10, further including a plurality of instructions that, when executed, cause the one or more processors to:
transmit the first treatment data to the first smart pill and the second treatment data to the second smart pill before the first smart pill and second smart pill are consumed by the respective first patient and second patient; and
transmit the modified first treatment data to the first smart pill or the modified second treatment data to the second smart pill after the first smart pill or the second smart pill is consumed by the respective first patient or second patient.

19. A method for managing treatment of patients using smart pills, the method comprising:
generating, by one or more processors, first treatment data usable by a first smart pill and second treatment data usable by a second smart pill, the first smart pill to control a release of a first drug from the first smart pill in a first patient, the second smart pill to control the release of the first drug from the second smart pill in a second patient;
transmitting, by the one or more processors, the first treatment data to the first smart pill and the second treatment data to the second smart pill;
obtaining, by the one or more processors and from the first smart pill, first physiological data associated with the first patient, wherein the first physiological data is in response to the release of the first drug from the first smart pill;
obtaining, by the one or more processors and from the second smart pill, second physiological data associated with the second patient, wherein the second physiological data is in response to the release of the first drug from the second smart pill;
performing, by the one or more processors, a first comparison of the first physiological data to third physiological data, the third physiological data being reference physiological data;
performing, by the one or more processors, a second comparison of the second physiological data to the third physiological data;
identifying, by the one or more processors, the first patient or the second patient as having a target physiological response based on the first comparison and the second comparison;
modifying, by the one or more processors, the first treatment data or the second treatment data associated with which of the first patient or the second patient did not have the target physiological response; and
transmitting the modified first treatment data or the modified second treatment data to the respective first smart pill or the second smart pill to cause release of at least one of a second drug or a different amount of the first drug.

20. The method of claim 19, further including adjusting, by the one or more processors, at least one of the first treatment data or the second treatment data based on one or more patient specific factors before transmitting at least one of the first treatment data to the first smart pill or the second treatment data to the second smart pill.

21. The method of claim 20, wherein the patient specific factors include patient health history data.

22. The method of claim 20, wherein the patient specific factors include patient schedule data.

23. The method of claim 20, wherein adjusting the at least one of the first treatment data or the second treatment data includes applying one or more heuristics to the patient specific factors.

24. The method of claim 19, further including transmitting the first treatment data to the first smart pill and the second treatment data to the second smart pill after the first and second smart pills are consumed by the first and second patient.

25. The method of claim 19, further including
transmitting the first treatment data to the first smart pill and the second treatment data to the second smart pill before the first smart pill and second smart pill are consumed by the respective first patient and second patient; and
transmitting the modified first treatment data to the first smart pill or the modified second treatment data to the second smart pill after the first smart pill or the second smart pill is consumed by the respective first patient or second patient.

\* \* \* \* \*